US010765321B2

(12) United States Patent
Kargar et al.

(10) Patent No.: US 10,765,321 B2
(45) Date of Patent: *Sep. 8, 2020

(54) IMAGE-ASSISTED DIAGNOSTIC EVALUATION (71) Applicant: Siemens Healthcare GmbH, Erlangen (DE)

(72) Inventors: Soroosh Kargar, Lake in the Hills, IL (US); Weng Lei, Mount Prospect, IL (US)

(73) Assignee: Siemens Healthcare GmbH, Erlangen (DE)

( * ) Notice: Subject to any disclaimer, the term of this patent is extended or adjusted under 35 U.S.C. 154(b) by 338 days.

This patent is subject to a terminal disclaimer.

(21) Appl. No.: 15/887,586

(22) Filed: Feb. 2, 2018

(65) Prior Publication Data

US 2018/0153405 A1 Jun. 7, 2018

Related U.S. Application Data (63) Continuation of application No. 13/929,909, filed on Jun. 28, 2013, now Pat. No. 9,931,038.

(Continued)

(51) Int. Cl.
*A61B 5/03* (2006.01)
*A61B 5/00* (2006.01)
(Continued)

(52) U.S. Cl.
CPC .......... *A61B 5/0037* (2013.01); *A61B 5/0035* (2013.01); *A61B 5/0044* (2013.01); *A61B 6/503* (2013.01); *A61B 6/545* (2013.01); *A61B 5/4848* (2013.01); *A61B 6/032* (2013.01); *A61B 6/037* (2013.01); *A61B 6/4441* (2013.01); *A61B 6/465* (2013.01); *A61B 6/487* (2013.01); *A61B 6/5235* (2013.01); *A61B 8/0883* (2013.01); *A61N 2005/1061* (2013.01)

(58) Field of Classification Search
CPC ....... A61B 5/0037; A61B 6/545; A61B 6/503; A61B 5/0035; A61B 5/0044; A61B 8/0883; A61B 6/5235; A61B 6/487; A61B 6/465; A61B 6/037; A61B 6/032; A61B 5/4848; A61B 6/4441; A61N 2005/1061
See application file for complete search history.

(56) References Cited

U.S. PATENT DOCUMENTS 7,991,450 B2 * 8/2011 Virtue .................... A61B 6/032
382/128
8,369,588 B2 * 2/2013 Dejon ...................... G06T 5/50
345/629

(Continued)

*Primary Examiner* — Sanjay Cattungal (57) ABSTRACT

Disclosed herein is a framework for facilitating image-assisted diagnostic evaluation. In accordance with one aspect of the framework, imaging parameters used in acquiring a treatment image of a portion of patient anatomy are automatically recorded during an imaging examination. The treatment image may indicate at least one location of at least one treated site. During a follow-up examination, a follow-up image of the portion of the patient anatomy may be automatically acquired using the recorded imaging parameters. To assist evaluation of treatment results, the treatment image with the indicated location of the treated site may be overlaid over the follow-up image.

23 Claims, 6 Drawing Sheets

Related U.S. Application Data

(60) Provisional application No. 61/665,343, filed on Jun. 28, 2012.

(51) Int. Cl.
*A61B 6/00* (2006.01)
*A61B 6/03* (2006.01)
*A61B 8/08* (2006.01)
*A61N 5/10* (2006.01)

(56) References Cited

U.S. PATENT DOCUMENTS

| | | | | |
|---|---|---|---|---|
| 2006/0244845 A1* | 11/2006 | Craig | G11B 27/034 | 348/231.3 |
| 2007/0167801 A1* | 7/2007 | Webler | G06T 19/00 | 600/459 |
| 2010/0232573 A1* | 9/2010 | Ozawa | A61B 6/04 | 378/95 |
| 2011/0096907 A1* | 4/2011 | Mohamed | G06T 11/005 | 378/98 |
| 2012/0250964 A1* | 10/2012 | Pfister | A61B 6/12 | 382/130 |
| 2019/0287241 A1* | 9/2019 | Hill | G06T 7/0012 | |

* cited by examiner

| C-Arm Angulation | C-Arm Rotation | Table Height | Table Position | Table Longitudinal Position | Table Horizontal Position | Stem Cell Marker Overlay Image | Treated sites |
|---|---|---|---|---|---|---|---|
| RAO27 | 26 CRAN | 90cm | 0 | 0 | 0 | #1 | #1 |
| RAO27 | 26 CRAN | 90cm | 0 | 0 | 0 | #1 | #2 |
| RAO27 | 26 CRAN | 90cm | 0 | 0 | 0 | #1 | #3 |
| RAO27 | 26 CRAN | 90cm | 0 | 0 | 0 | #1 | #4 |
| RAO27 | 26 CRAN | 90cm | 0 | 0 | 0 | #1 | #5 |
| RAO27 | 26 CRAN | 90cm | 0 | 0 | 0 | #1 | #6 |
| LAO41 | 26 CRAN | 90cm | 0 | 0 | 0 | #2 | #1 |
| LAO42 | 27 CRAN | 90cm | 0 | 0 | 0 | #2 | #2 |
| LAO43 | 28 CRAN | 90cm | 0 | 0 | 0 | #2 | #3 |

IMAGE-ASSISTED DIAGNOSTIC EVALUATION

CROSS-REFERENCE TO RELATED APPLICATION

This application is a continuation of U.S. non-provisional application Ser. No. 13/929,909 filed Jun. 28, 2013, which claims the benefit of U.S. provisional application No. 61/665,343 filed Jun. 28, 2012, the entire contents of which are incorporated herein by reference.

TECHNICAL FIELD

The present disclosure generally relates to systems and methods for facilitating image-assisted diagnostic evaluation.

BACKGROUND

Stem cells are naturally used by the human body to facilitate healing damaged tissues. When a human body is injured, stem cells travel to an injured site and transform themselves into the type of cells damaged to substitute for the damaged cells. Stem cells are able to renew themselves through mitotic cell division and to differentiate into a diverse range of specialized cell types. Overall, stem cells do a good job to heal most damage. Unfortunately, for heart disease cases, stem cells do not completely repair damaged heart tissue. Therefore, stem cell therapy for heart disease is performed in hospitals.

Stem cell therapy for heart disease is a relatively new procedure that is commonly carried out in an angiography x-ray laboratory. A physician typically uses a known angiography system in stem cell therapy. In known systems, a physician performs fluoroscopy to find a damaged heart tissue site of a patient and injects stem cells at the site. The location of the site of stem cell injection is marked on a film that is manually placed on top of an x-ray monitor. This film is used to record the location of the stem cell treatment location. It is used in a follow-up visit to check treatment results.

In a follow-up visit, the film that was previously used to record the stem cell injection site is placed on top of a display monitor showing a current image of the stem cell injection site to evaluate the therapy result. This is a cumbersome and error-prone procedure that is vulnerable to misalignment of the film and misidentification of a site in the current image.

As such, there is a need for an improved framework that addresses these deficiencies and related problems.

SUMMARY

The present disclosure relates to a framework for facilitating image-assisted diagnostic evaluation. In accordance with one aspect of the framework, imaging parameters used in acquiring a treatment image of a portion of patient anatomy are automatically recorded during an imaging examination. The treatment image may indicate at least one location of at least one treated site. During a follow-up examination, a follow-up image of the portion of the patient anatomy may be automatically acquired using the recorded imaging parameters. To assist evaluation of treatment results, the treatment image with the indicated location of the treated site may be overlaid over the follow-up image.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, X-ray imaging data may be used herein as an exemplary imaging modality. It will be appreciated, however, that data from any type of imaging modality including but not limited to magnetic resonance imaging (MM), computed tomography (CT), positron emission tomography (PET), PET-CT, single-photon emission computed tomography (SPECT), SPECT-CT, MR-PET, ultrasound images or the like may also be used in various embodiments of the invention.

Unless stated otherwise as apparent from the following discussion, it will be appreciated that terms such as "segmenting," "generating," "registering," "determining,"

"aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using a computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from R3 to R or R7, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The following description sets forth one or more implementations for facilitating image-assisted diagnostic evaluation. One aspect of the present framework facilitates image-assisted diagnostic evaluation of anatomical site-specific treatment, such as checking for heart muscle recovery after stem cell treatment. In one implementation, during an imaging examination, imaging parameters that are used for acquiring a treatment image of a portion of patient anatomy (e.g., heart) are automatically recorded. Such imaging parameters may include, but are not limited to, C-arm angulation and patient support table position indicative parameters. The treatment image may be marked to indicate the locations of the treated sites, such as stem cell injection sites.

During a subsequent follow-up imaging examination, the user (e.g., physician) may retrieve the same study that was used in the previous imaging examination. In response to the user's selection of a function (e.g., follow-up button for last stem cell therapy), the recorded imaging parameters may be retrieved. The C-arm and patient support table may be automatically adjusted based on the recorded imaging parameters to acquire a follow-up image of the same patient anatomy. During fluoroscopy, the user may select a function to check treatment results. In response to the user's selection, the framework may automatically overlay the treatment image with the indicated location of the treated site over the follow-up image. The user may then check the resulting image to determine if the treatment is successful (e.g., heart muscle is moving).

It is understood that while a particular application directed to diagnostic evaluation of a coronary stem cell treatment may be shown, the technology is not limited to the specific embodiments illustrated. For example, the present technology has application to image-assisted diagnostic evaluation of other types of treatments.

Figure 1:
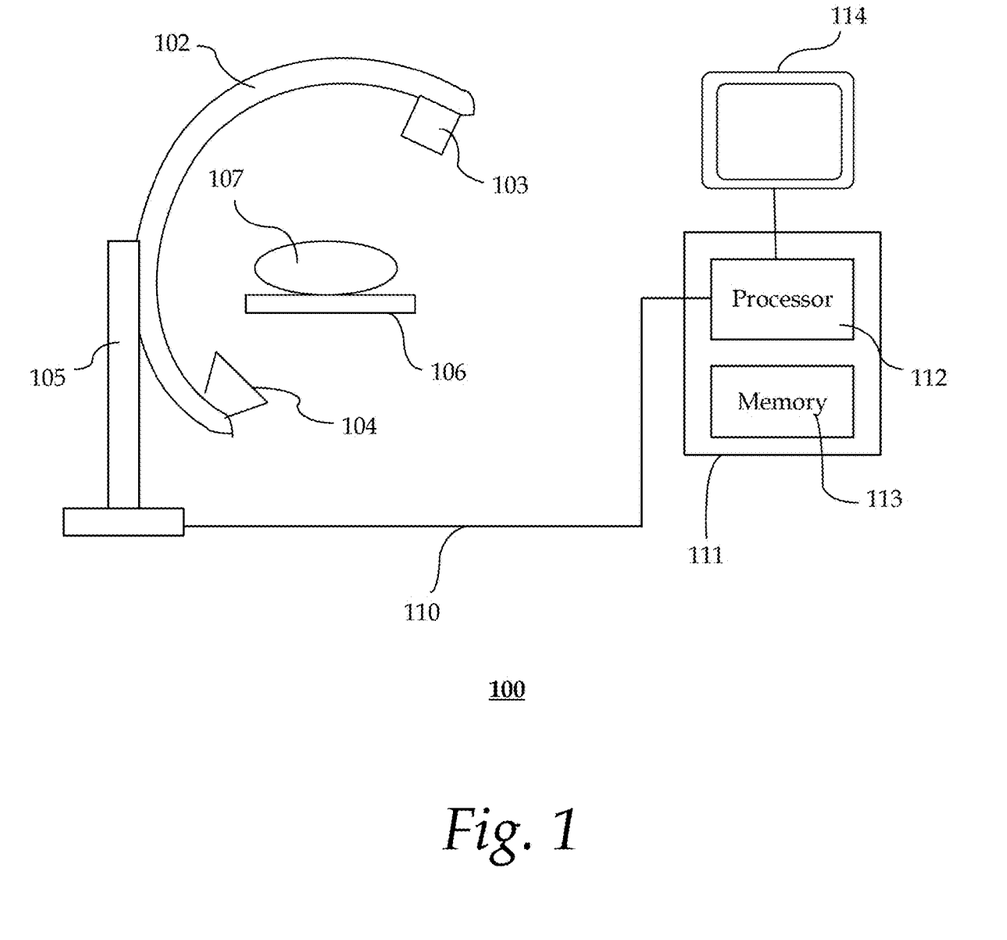
FIG. 1 shows an exemplary system for image-assisted diagnostic evaluation.

FIG. 1 shows an exemplary system 100 for image-assisted diagnostic evaluation. System 100 may be an X-ray angiography system that includes C-arm 102 that serves as an intraoperative x-ray control. An x-ray source 103 and an x-ray detector 104 are incorporated at the ends of the C-arm 102. The C-arm 102 is movably mounted on a stand 105, and can thus be displaced about a patient support table (or bed) 106. Positioned on the bed 106 is a patient 107, on whom, for instance, a stem cell treatment (or therapy), an imaging examination and subsequent follow-up examination are to be carried out.

The processing of the x-ray images (or fluoroscopic images) recorded with the C-arm 102 may be carried out by processing unit 111 in accordance with the present framework as described herein. Processing unit 111 may be a desktop personal computer, a portable laptop computer, another portable device, a mini-computer, a mainframe computer, a server, a storage system, a dedicated digital appliance, a communication device, or another device having a storage sub-system configured to store a collection of digital data items. In some implementations, processing unit 111 operates as a standalone device. In other implementations, processing unit 111 may be connected (e.g., using a network) to other machines, such as a workstation (not shown). In a networked deployment, processing unit 111 may operate in the capacity of a server, a client user machine in a server-client user network environment, or as a peer machine in a peer-to-peer (or distributed) network environment. The processing unit 111 may be coupled to display device 114, input devices (not shown), and/or other peripheral devices, including but not limited to, additional data storage devices and printing devices.

The processing unit 111 comprises a processor 112 (or central processing unit) and a memory (or non-transitory computer-readable media) 113. The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in memory 113. Memory 113 may include random access memory (RAM), read only memory (ROM), magnetic floppy disk, flash memory, and other types of memories, or a combination thereof. The computer-readable program code is executed by processor 112 to process images (e.g., x-ray images) acquired by an imaging device (e.g., x-ray gantry 103, 104). As such, the processing unit 111 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different memory 113 may be used for storing image data, imaging parameters, visualization instructions, knowledge base, individual patient data, etc. Such data may also be stored in external storage or other memories (not shown). The external storage may be implemented using a database management system (DBMS) managed by the processor 112 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

In some implementations, the image data recorded with the x-ray gantry 103, 104 is transmitted via a data cable 110 to the processor 112. The processor 112 may serve as an acquisition processor to automatically record imaging parameters used in acquiring the image data. The imaging parameters may be stored in, for example, memory 113. In some implementations, the processor 112 may also serve as an image processor for using the recorded imaging parameters during a follow-up examination to acquire follow-up image data and to assist evaluation of treatment results. It should be appreciated that the acquisition processor and the image processor may be implemented using the same or different processors 112.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

Figure 2:
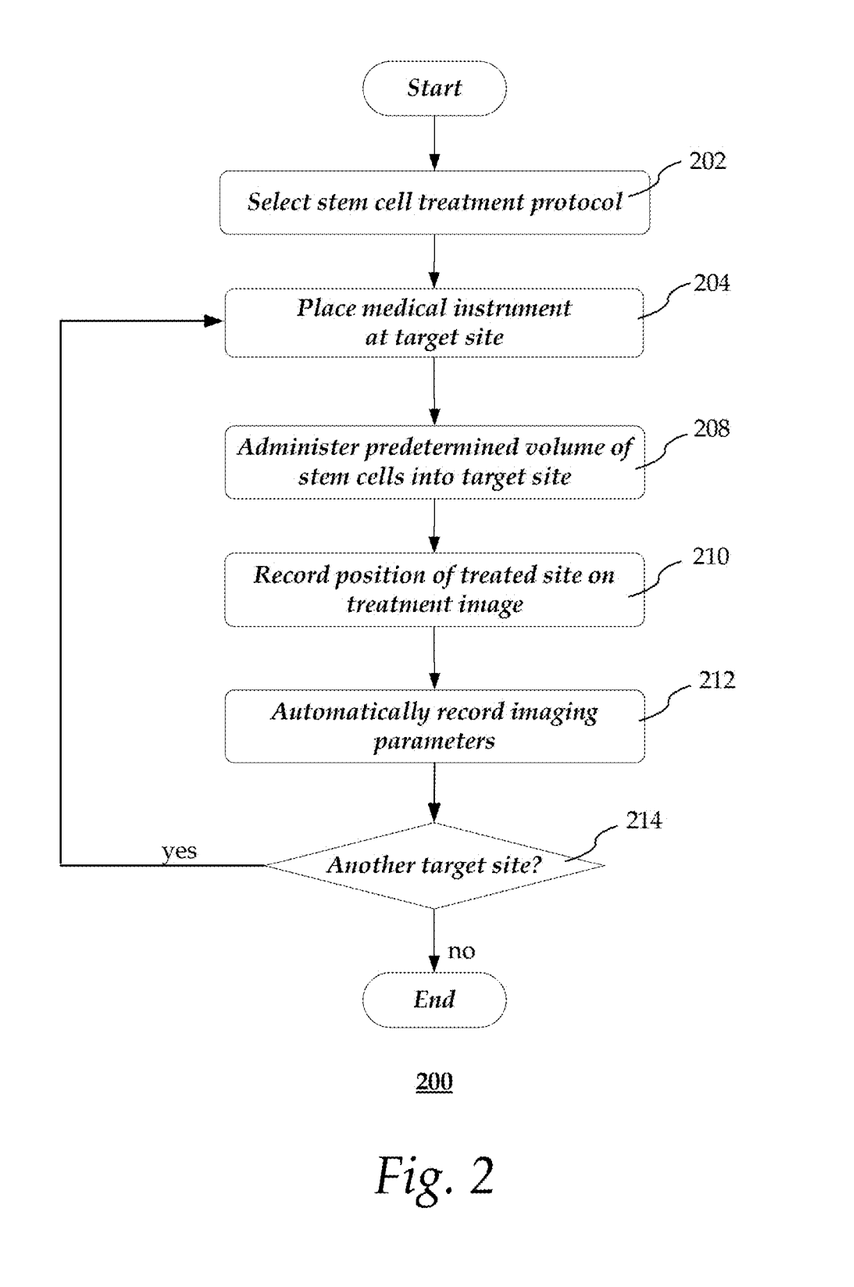
FIG. 2 shows an exemplary stem cell treatment workflow.

FIG. 2 shows an exemplary stem cell treatment workflow 200. The exemplary method 200 may be implemented at least in part by, for instance, the processing unit 111, as previously described with reference to FIG. 1.

At 202, the user (e.g., physician) selects a stem cell treatment protocol for the imaging examination. In some implementations, the system 100 provides a user friendly stem cell fluoroscopy therapy protocol. Other types of protocols are also useful. Fluoroscopy generally refers to an imaging technique that uses X-rays to obtain moving images of internal structures of a patient through the use of a fluoroscope (e.g., X-ray source 103 and detector 104). The user (e.g., physician) may use the selected protocol to perform fluoroscopy for patient therapy. Prior to performing the fluoroscopy, the user may move the patient support table 106 and the C-arm 102 to a desired position for patient therapy and treatment.

At 204, a medical instrument is placed at a target site. The medical instrument may be, for example, a catheter, biopsy needle, endoscope, laparoscope, or any other types of medical instruments for administering a treatment. The target site (or treatment site) is located at a part of the patient's body where treatment is desired. In the case of coronary stem cell therapy, the target site may be at, for example, the left atrium wall.

At 208, a predetermined volume of stem cells is administered into the target site via the medical instrument. Stem cells may be injected via a catheter needle through an opening at the target site. Other methods of administering stem cells may also be used. Stem cells may be administered so as to repair a damaged or diseased tissue (e.g., cardiac tissue) of the patient 107.

Figure 3:
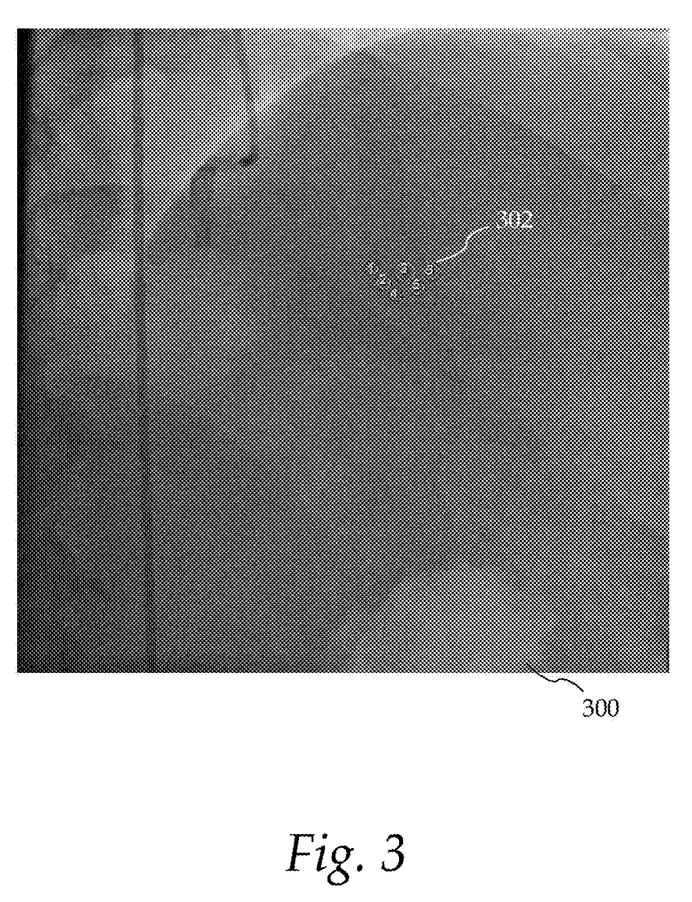
FIGS. 3 and 4 show exemplary treatment images.
Figure 4:
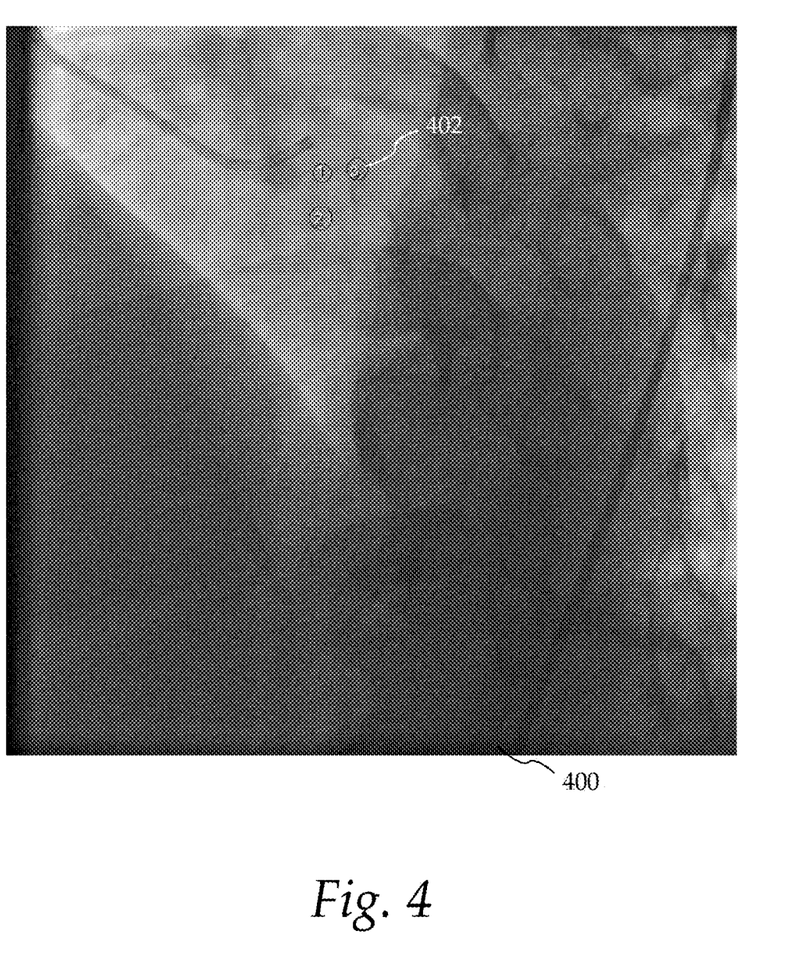

At 210, the position of the treated site may be recorded on a treatment image. The treatment image may be acquired via, for instance, the x-ray gantry 103, 104 incorporated in the C-arm 102. In some implementations, the treatment image is a fluoroscopic image. Other types of images are also useful. The treatment image may be presented on display device 114. A user may mark the treated location on the treatment image via, for instance, a user interface presented on the display device 114. FIG. 3 shows an exemplary treatment image 300. The treatment image 300 includes markings 302 indicating the locations of 6 treated target sites. FIG. 4 shows another exemplary treatment image 400. The treatment image 400 includes markings 402 indicating the locations of 3 treated target sites.

The treatment image may also include other information, such as patient's information (e.g., name, age, gender, etc.), time of image acquisition, room number, x-ray information, height of patient support table, and so forth. Such information may be stored in, for instance, a Digital Imaging and Communications in Medicine (DICOM) header associated with the treatment image.

Returning to FIG. 2, at 212, the processor 112 may automatically record imaging parameters that were used to acquire the treatment image. Such imaging parameters may include, but are not limited to, C-arm angulation, C-arm rotation, and patient support table position indicative parameters (e.g., longitudinal position, horizontal position, height, etc.). Other types of imaging parameters may also be recorded. The treatment image and the imaging parameters may be stored in, for instance, memory 113. Steps 210 and 212 may be repeated if there is a change in imaging parameters or a new treatment image is acquired. The automatic recording is terminated as soon as the physician completes the treatment process.

At 214, the physician determines if there is another target site to be treated. If there is another target site, steps 204-212 are repeated. If no other target site is to be treated, the process 200 terminates.

Figure 5:
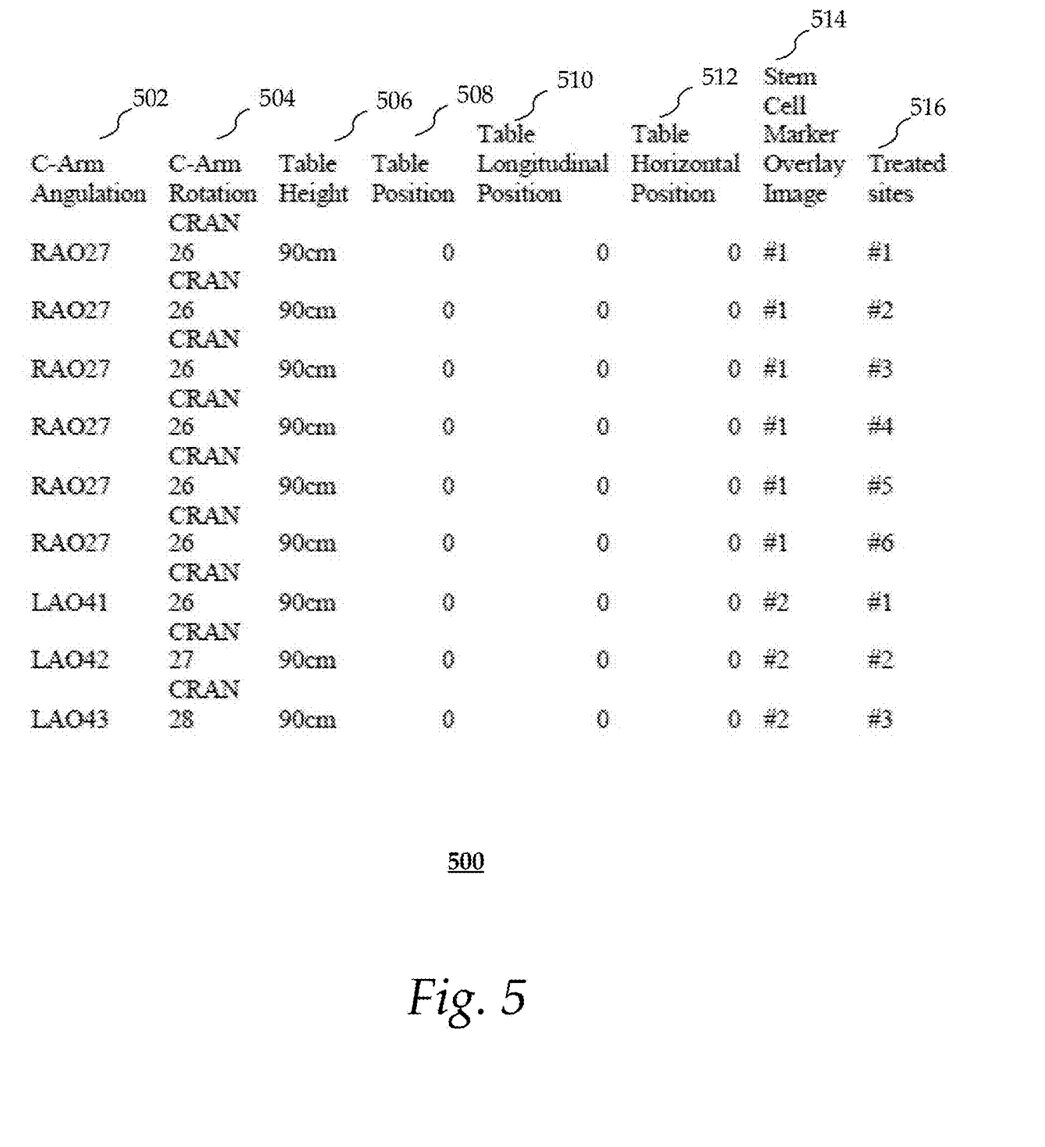
FIG. 5 shows an exemplary look-up table.

FIG. 5 shows an exemplary look-up table 500 that may be generated by process 200 after all the target sites have been treated. As shown, the location of each treated target site 516 is recorded in association with imaging parameters (i.e., c-arm angulation 502, c-arm rotation 504, table height 506, table position 508, table longitudinal position 510, table horizontal position 512) and the corresponding stem cell marker overlay image (or treatment image) 514 acquired during the imaging examination. The table 500 may be used to generate images during a follow-up visit, as will be discussed in more detail in connection with FIG. 6.

Figure 6:
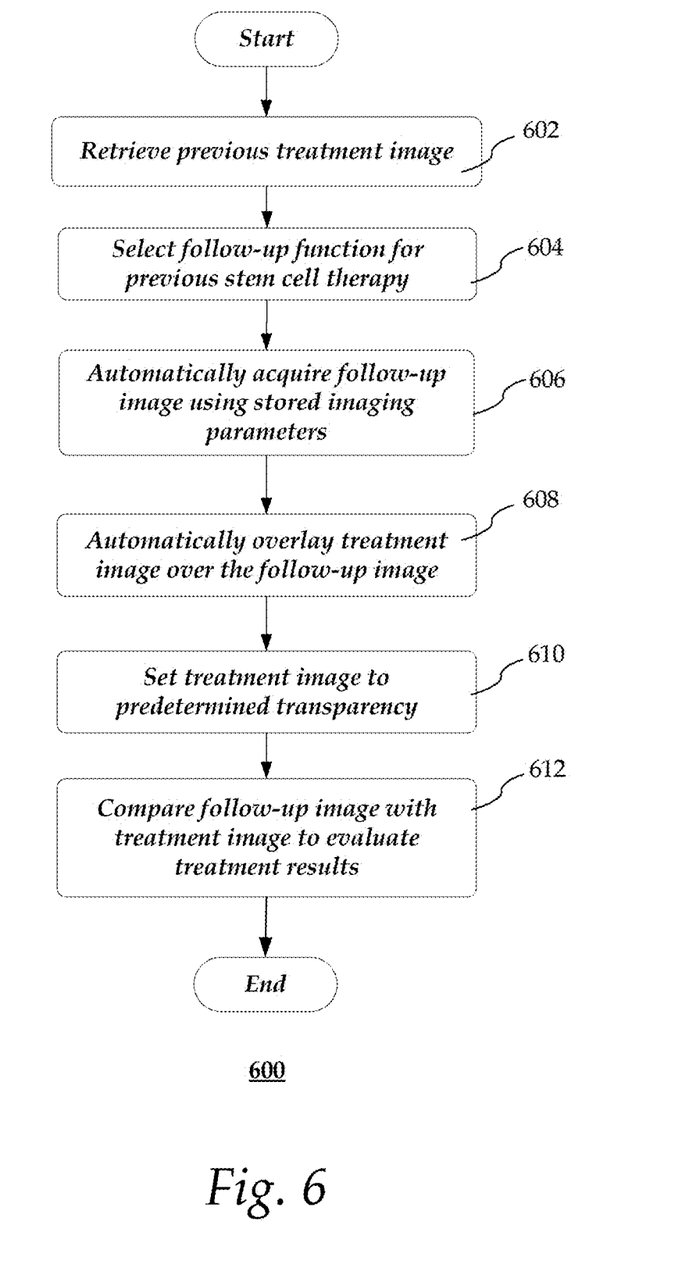
FIG. 6 shows an exemplary stem cell treatment follow-up visit workflow.

FIG. 6 shows an exemplary stem cell treatment follow-up visit workflow. The exemplary method 600 may be implemented at least in part by, for instance, the processing unit 111, as previously described with reference to FIG. 1.

At 602, the processor 112 retrieves a treatment image from the memory 113. The treatment image may have been acquired during a previous stem cell treatment workflow, such as workflow 200 as previously described with reference to FIG. 2. As discussed previously, the treatment image may indicate the location of at least one site treated during the last examination.

At 604, the user may select a "follow up" function (e.g., button, menu item, etc.) to access the last stem cell therapy. The user interface may be presented on display device 114. In response to the user selection, the processor 112 may automatically retrieve stored imaging parameters (e.g., C-arm angulation, patient table support position etc.) associated with the treatment image.

At 606, the processor 112 automatically acquires a follow-up image of a portion of the patient's anatomy. The follow-up image may be acquired using the same imaging parameters (e.g., C-arm angulation and table position) as the previous imaging examination. For instance, the processor 112 may automatically adjust the C-arm 102 and patient table 106 to the C-arm angulation and table position indicated by the stored imaging parameters. The follow-up image may then be acquired by, for instance, fluoroscopy using, the x-ray gantry 103, 104 incorporated in the C-arm 102.

At 608, the processor 112 automatically overlays the treatment image with the indicated location of the treated site over the follow-up image to generate a composite image. This may be performed in response to the user selecting, for instance, a "Check stem cell therapy result" function via the user interface presented on display device 114 during fluoroscopy.

At 610, the treatment image is set to a predetermined transparency (e.g., 50%) in the composite image. This allows the user to identify locations of the treated sites on the follow-up image.

At 612, the user compares the follow-up image with the treatment image to evaluate treatment results. Treatment results may be evaluated by, for example, detecting any mechanical movement of the heart muscle at or near the treated site. If the heart muscle at the treated site is moving, the therapy is determined to be successful. Otherwise, the therapy is determined to have failed.

Steps 606-612 may be repeated to check remaining treated sites in images that were obtained with different imaging parameters.

A processor as used herein is a device for executing machine-readable instructions stored on a computer readable medium, for performing tasks and may comprise any one or a combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general-purpose computer or special-purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other devices.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other devices. The functions and process steps herein may be performed automatically or wholly or partially in response to a user command. An activity (including a step) performed automatically is performed in response to executable instruction or device operation without direct user initiation of the activity.

The system and processes of the Figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of the system. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. An imaging system for image-assisted diagnostic evaluation, comprising:
   an acquisition processor configured to automatically record in a look-up table, relating to an imaging examination, at least one location of at least one treated site in association with imaging parameters used in acquiring a treatment image of a portion of patient anatomy, wherein the treatment image includes the at least one location of the at least one treated site, wherein the look-up table associates the imaging parameters with the treatment image and the location of the at least one treated site;
   memory configured to store the look-up table and the treatment image; and
   an image processor configured to use, during a follow-up examination, the recorded imaging parameters in the look-up table to set parameters for acquisition of a follow-up image of the portion of the patient anatomy, set the treatment image to a predetermined transparency, overlay the treatment image over the follow-up image and compare the follow-up image with the treatment image to evaluate treatment results.

2. The system according to claim 1, wherein the imaging parameters comprise at least one C-arm angulation indicative parameter.

3. The system according to claim 1, wherein the imaging parameters comprise at least one patient support table position indicative parameter.

4. The system according to claim 1, wherein the image processor is configured to, during the follow-up examination, adjust a C-arm and a patient support table according to the recorded imaging parameters to acquire the follow-up image.

5. The system according to claim 1, wherein the treated site comprises a stem cell injection site.

6. The system according to claim 1, wherein the patient anatomy comprises a heart.

7. The system according to claim 1, wherein the treatment image comprises a fluoroscopic image.

8. The system according to claim 1, wherein the treatment image comprises an X-ray, magnetic resonance imaging (MRI), computed tomography (CT), positron emission tomography (PET), PET-CT, single-photon emission computed tomography (SPECT), SPECT-CT, MR-PET or ultrasound image.

9. The system according to claim 1, wherein the follow-up image comprises a fluoroscopic image.

10. The system according to claim 1, wherein the follow-up image comprises an X-ray, magnetic resonance imaging (MRI), computed tomography (CT), positron emission tomography (PET), PET-CT, single-photon emission computed tomography (SPECT), SPECT-CT, MR-PET or ultrasound image.

11. The system according to claim 1, wherein the acquisition processor is configured to repeat, in response to a change in the imaging parameters, automatically recording the at least one location of the at least one treated site in association with the imaging parameters.

12. The system according to claim 1, wherein the imaging examination occurs during treatment of a patient and the acquisition processor automatically terminates recording at the end of the treatment.

13. The system according to claim 5, wherein the patient anatomy comprises a heart and wherein the image processor compares the follow-up image with the treatment image by detecting any muscle movement at or near the treated site at the heart in the follow-up image.

14. The system according to claim 1, further comprising:
   a user interface for providing to a user the capability to mark the at least one location of the at least one treated site.

15. A method of supporting image-assisted diagnostic evaluation from a computer system, comprising:
   automatically recording in a look-up table, relating to an imaging examination, at least one location of at least one treated site in association with imaging parameters used in acquiring a treatment image of a portion of patient anatomy, wherein the treatment image includes the at least one location of the at least one treated site, wherein the look-up table associates the imaging parameters with the treatment image and the location of the at least one treated site;
   automatically associating the image parameters with the indication of the at least one location;
   using the recorded imaging parameters in the look-up table to set parameters for acquisition, during a follow-up examination, of a follow-up image of the portion of the patient anatomy; and
   evaluating treatment results by setting the treatment image to a predetermined transparency, overlaying the treatment image over the follow-up image, and comparing the follow-up image with the treatment image.

16. The method according to claim 15, wherein the step of automatically recording the at least one location of the at least one treated site in association with the imaging parameters is repeated in response to a change in the imaging parameters.

17. The method according to claim 15, wherein comparing the follow-up image with the treatment image comprises detecting any muscle movement at or near the treated site at the heart in the follow-up image.

18. The method according to claim 15, wherein the imaging parameters comprise C-arm angulation and patient support table position indicative parameters.

19. The method according to claim 15, wherein acquisition of the follow-up image comprises automatically adjusting a C-arm and a patient support table according to the recorded imaging parameters to acquire the follow-up image.

20. The method according to claim 15, wherein the treated site comprises a stem cell injection site.

21. A non-transitory computer readable medium embodying a program of instructions executable by machine to perform steps for supporting image-assisted diagnostic evaluation, the steps comprising:
   automatically recording in a look-up table, relating to an imaging examination, at least one location of at least one treated site in association with imaging parameters used in acquiring a treatment image of a portion of patient anatomy, wherein the treatment image includes the at least one location of the at least one treated site, wherein the look-up table associates the imaging parameters with the treatment image and the location of the at least one treated site;
   automatically associating the imaging parameters with the indication of the at least one location;
   using the recorded imaging parameters in the look-up table to set parameters for acquisition, during a follow-up examination, of a follow-up image of the portion of the patient anatomy; and
   evaluating treatment results by setting the treatment image to a predetermined transparency, overlaying the treatment image over the follow-up image, and comparing the follow-up image with the treatment image.

22. The non-transitory computer readable medium according to claim 21, wherein the comparing the follow-up image with the treatment image comprises detecting any muscle movement at or near the treated site at the heart in the follow-up image.

23. The non-transitory computer readable medium according to claim 21, wherein the imaging parameters comprise C-arm angulation and patient support table position indicative parameters.

\* \* \* \* \*